United States Patent [19]

Lackie

[11] Patent Number: 5,554,340
[45] Date of Patent: *Sep. 10, 1996

[54] ASSAY SYSTEM

[75] Inventor: Steve J. Lackie, Lexington, Mass.

[73] Assignee: Sapidyne, Inc., Boise, Id.

[*] Notice: The term of this patent shall not extend beyond the expiration date of Pat. No. 5,372,783.

[21] Appl. No.: 546,657

[22] Filed: Oct. 23, 1995

Related U.S. Application Data

[63] Continuation of Ser. No. 265,648, Jun. 24, 1994, which is a continuation of Ser. No. 924,720, Aug. 3, 1992, Pat. No. 5,372,783.

[51] Int. Cl.$^6$ ................................................. G01N 21/00
[52] U.S. Cl. ................. 422/68.1; 422/82.07; 422/82.08; 422/82.05; 436/546; 436/547; 436/527; 436/538; 436/805; 435/808; 356/246
[58] Field of Search ............................ 422/82.07, 82.08, 422/82.05, 68.1, 99, 104, 102; 55/387, 485; 359/665; 436/164–165, 172, 527, 538, 531, 546–547, 805; 435/808; 356/246, 417, 410, 440

[56] References Cited

U.S. PATENT DOCUMENTS

| | | | |
|---|---|---|---|
| 1,716,321 | 5/1927 | Pearson | 359/665 |
| 2,978,718 | 10/1951 | Gross | 55/485 |
| 3,002,092 | 9/1961 | Cary | 501/40 |
| 3,025,142 | 3/1962 | Williams | 55/387 |
| 3,492,396 | 1/1970 | Dalton et al. | 424/12 |
| 3,600,063 | 8/1971 | Bowen | 359/665 |
| 4,059,685 | 11/1977 | Johnson | 436/527 |
| 4,153,675 | 5/1979 | Kleinerman | 422/56 |
| 4,173,392 | 11/1979 | Ekinaka et al. | 264/1.5 |
| 4,268,171 | 5/1981 | Sternberg | 356/341 |
| 4,348,107 | 9/1982 | Leif | 356/246 |
| 4,425,438 | 1/1984 | Bauman et al. | 436/527 |
| 4,469,787 | 9/1984 | Woods et al. | 422/61 |
| 4,505,260 | 3/1985 | Metzger | 359/665 |
| 4,585,623 | 4/1986 | Chandler | 422/57 |
| 4,652,533 | 3/1987 | Jolley | 436/518 |
| 4,678,268 | 7/1987 | Russo et al. | 264/1.5 |
| 4,713,347 | 12/1987 | Mitchell et al. | 422/68 |
| 4,714,345 | 12/1987 | Schrader | 356/246 |
| 4,775,515 | 10/1988 | Cottingham | 422/73 |
| 4,780,423 | 10/1988 | Bluestein et al. | 436/527 |
| 4,912,051 | 3/1990 | Zaromb | 436/178 |
| 5,120,643 | 6/1992 | Ching et al. | 422/59 |
| 5,372,783 | 12/1994 | Lackie | 422/68.1 |

FOREIGN PATENT DOCUMENTS 404258   12/1990   European Pat. Off. .

OTHER PUBLICATIONS

Friguet et al., "Measurements of the true affinity constant in solution of antigen–antibody complexes by enzyme–linked immunosorbent assay", Jour. of Immun. Methods, 77, pp. 305–319, 1985.

Pollema et al., "Sequential injection immunoassay utilizing immunomagnetic beads", Anal. Chem. 64, pp. 1356–1361, 1992.

Freytag et al., "Affinity–Column–Mediated Immunoezymometric Assays: Influence of Affinity–Column Ligand and Valency of Antibody–Enzyme Conjugates", Clin. Chem., V. 30, No. 9, 1494–1498, 1984.

(List continued on next page.)

Primary Examiner—Robert J. Warden
Assistant Examiner—Hien Tran
Attorney, Agent, or Firm—Choate, Hall & Stewart

[57] ABSTRACT

A system for assaying a fluid sample, typically employing a fluorescent tag, the system comprising a lens capable of focussing both excitation and fluorescent radiation, a fluid-flow conducting conduit being provided in the lens extending transversely of the optical axis of and through the focal region of the latter. One or more mechanical screens are disposed adjacent to the focal region in the conduit to arrest passage of beads as a function of bead diameter. The beads, precoated with at least a moiety of a ligand/conjugate complex, e.g. a specific-binding ligand, are preferably substantially transparent to both the excitation and fluorescent radiation.

14 Claims, 2 Drawing Sheets

OTHER PUBLICATIONS

Freytag et al., "A Highly Sensitive Affinity–Column–Mediated Immunometric Assay, as Exemplified by Digoxin", Clin. Chem., V. 30, No. 3, 417–420, 1984.

Glaser, "Antigen–Antibody Binding and Mass Transport by Convection and Diffusion to a Surface: A Two–Dimensional Computer Model of Binding and Dissociation Kinetics", Anal. Biochem., V. 213, 152–161, 1993.

Hudson, "Infrared Systems Engineering", Wiley–Interscience, 1969.

Jolley et al., "Particle Concentration Fluorescence Immunoassay (PCFIA); A New Rapid Immunoassay Technique with High Sensitivity", Journal of Immunological Methods, vol. 67, 21–35, 1984.

O'Shannessy et al., "Determination of Rate of Equilibrium Binding Constants for Macromolecular Interactions Using Surface Plasmon Resonance: Use of Nonlinear Least Squares Analysis Methods", Anal. Biochem, V. 212, 457–468, 1993.

Ordentlich et al., 1988, "Rhizospshere Colonization by *Serratia marcescens* for control of *Sclerotium rolfsii*, Soil. Biol. Biochem.," 19: 747–751.

Plant et al., "Liposome Enhanced Flow Injection Immunoanalysis", Biotechnology, vol. 6, 266–269, Mar. 1988.

Warren J. Smith, "Modern Optical Engineering. The Design of Optical Systems", McGraw–Hill, Inc. (pubs) ©1966.

ASSAY SYSTEM

This is a continuation of copending application Ser. No. 08/265,648 filed on Jun. 24, 1994, which is a continuation of Ser. No. 07/924,720, filed Aug. 3, 1992, now U.S. Pat. No. 5,372,783.

This invention relates to chemical and biochemical assays, and more particularly to an improved optical apparatus and methods for fluorescent assays.

Assays in which aliquots of sample-under-test and one or more reagents are variously reacted in highly specific reactions to form ligand/conjugate complexes such as antigen/antibody or similar complexes which may then be observed in order to assay the sample for a titer of a predetermined moiety from the sample, are well known. Typically, an antibody is used to assay for the presence of an antigen for which the antibody is specific, but such assays have been extended to quantitate haptens such as hormones, alkaloids, steroids, antigens, antibodies, nucleic acids, and fragments thereof, and it is in this broad sense that the term "ligand/conjugate" as used herein should be understood.

Sensitive immunoassays typically use tracer techniques in which a tagged constituent of the complex is incorporated, for example in the reagent, the non-complexed tagged reagent then being separated from the complexed reagent. The complexed can be thereafter quantitated by observing a signal from the tag. Radioisotopes, fluorescent and chemiluminescent molecules, colorimetric tags, and other markers have been used to label constituents or moieties of the complex, appropriate apparatus being employed to detect and measure the radiation from the label.

In such assays where at least one component of the conjugate complex is initially bound to a solid substrate preparatory to formation of the complex, a basic problem arises because of the typically lengthy time required to bind that component to the substrate. For example, fluorescent assays such as those performed in the usual 96 well microtiter plate, require time in the order of hours for binding of a component to the solid phase to occur notwithstanding such expedients as heating, shaking and the like. It will be appreciated that by increasing the surface area of the solid phase made available to binding or coating with a ligand, the binding delay may be considerably reduced. Consequently, the prior art relating to such solid phase assays (such as microtiter well assays, dipstick assays and the like) also teaches using small particles or beads as the solid phase.

Flowing the sample through a packed particulate bed speeds reactions between the sample ligand being assayed and a conjugate immobilized on the surface of the particles. Several factors probably contribute to this enhanced reactivity: the reduced diffusion distance, the constant stirring of sample due to turbulent flow, and the high density of binding sites in the reaction volume due to the high surface area exposed.

Known particle assays include the well-known bead agglutination test including quantitative or semiquantitative slide agglutination and techniques in which the agglutinated beads are separated from non-agglutinated beads by passage through a mechanical filter. Another known particle assay is that described in U.S. Pat. No. 4,780,423 in which particles with controlled porosity having ligand immobilized thereon are incubated in suspension and washed. Washing can involve sedimentation and resuspension of the particles. The resulting fluorescence can be read either from the concentrated or the suspended particles. In yet another known assay, the particles are bound to a membrane or filter through which the sample is then poured. This technique, is believed to have been limited to enzyme-colorimetric detection. Where the particles are incubated in a water suspension, the average diffusion distances which the free ligand in the sample must traverse and the time required to bring complex formation to completion tend to be quite large.

A principal object of the present invention is therefore to provide an improved optical assay system in which the kinetics and sensitivity are improved by increasing the surface area of the solid phase, decreasing diffusion distances, and enhancing the optical coupling among the solid phase to the excitation light source and the coupling of the solid phase to the detector. Another object of the present invention is to provide a novel flow cell that provides the desired enhancement between the sample and a detector. Yet other objects of the present invention are to provide such an assay system that requires small sample volume and is particularly suitable for assay of whole blood; to provide such an assay system in which the ligand/conjugate reaction is confined within a disposable item that is readily insertable and removable from the optical system of the flow cell; and to provide such an assay system in which all of the components of the desired complex other than the sample moiety to be assayed, are preprovided.

Other objects of the present invention will in part be obvious and will in part appear hereinafter. Generally, the foregoing and other objects of the present invention are achieved by a system for assaying a fluid sample, typically employing a tag or label intended to emit electromagnetic radiation when excited, the system comprising a flow cell comprising hollow, light-transparent conduit means adapted for fluid flow therethrough, and one or more separate porous masses of light-transparent material disposed in the conduit means, the porosity of the mass of transparent material being selected to permit fluid flow of the sample therethrough, at least a moiety of a respective ligand/conjugate complex e.g. a specific-binding ligand, being immobilized, as by precoating, on the surfaces of each mass.

In one embodiment, the mass comprises a plurality of particles preferably substantially transparent to light, particularly, where the complex formed includes a fluorescent label, transparent to both radiation required to excite fluorescence and the excited fluorescence. The particles are typically beads dimensioned within a specified range of diameters and can be preformed, as by sintering or the like. Alternatively, the mass can be formed by accretion against a fluid-porous barrier means disposed in the conduit means. In the latter case, the barrier means is disposed within the conduit means so as to define at least one wall of a chamber, the porosity of the barrier means being sufficiently smaller than said range so that particles entrained in a fluid flow through the conduit means are trapped by the barrier means and accrete to form the porous mass in the chamber.

A preferred embodiment of the present invention includes focussing optical lens means through which the conduit means forms a hollow, tubular passage extending transversely to the optical axis of and through the focal region of the lens means. Typically, the lens means comprises a plurality of lenses and the conduit means extends through one of those lenses. Where the system is to be used with a tag or label intended to emit electromagnetic radiation when excited, the lens means must be capable of focussing both the excitation and the emission radiation.

The invention accordingly comprises the apparatus possessing the construction, combination of elements and arrangement of parts, and the method comprising the several steps and the relation of one or more of such steps with respect to each of the others, all as exemplified in the following detailed disclosure, and the scope of the application of which will be indicated in the claims.

BRIEF DESCRIPTION OF THE DRAWINGS

In FIG. 1 there is shown exemplary apparatus 20 for assaying a fluid sample and which may typically employ an optical system including light source 22 for providing excitation radiation, light detector 24 for detecting light stimulated by the excitation radiation, beam splitter means such as dichroic or semitransparent mirror 26 and collimator means 28. The embodiment of FIGS. 1, 2 and 3 will be described, for ease of exposition, for use particularly in the context of fluorescence immunoassay, but it should be understood is not so limited. The term "light" as used herein will be understood to include wavelengths in the visible spectrum as well as those in the near infra-red and ultraviolet as well. Similarly, the term "excitation" will be understood to include excitation of fluorescence, polarized or not, as by radiation, excitation of chemiluminescence by chemical agents, emission by reflection of light from chromogens, and the like. In FIG. 2, reference numeral 56 points out the center of curvature of the solid focussing lens means 33.

Figure 1:
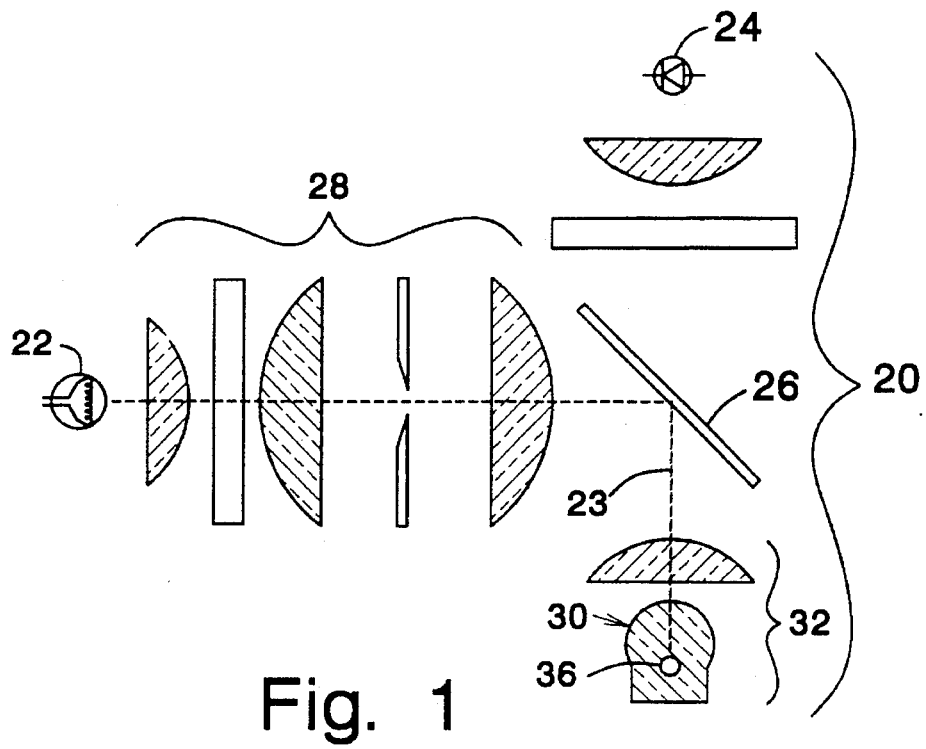
FIG. 1 is a diagrammatic representation, in cross-section, of assay apparatus embodying the principles of the present invention.
Figure 2:
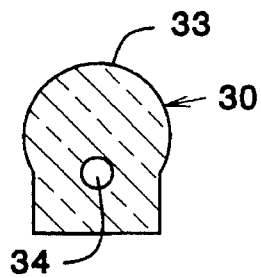
FIG. 2 is a schematic cross-section of one embodiment of the flow cell of the present invention.

The foregoing elements of the optical system are typically disposed in a frame (not shown) in fixed optical relationship to one another, as described more fully hereinafter. The invention further includes a flow cell 30, shown particularly in enlarged form in FIGS. 2 and 3, and in this embodiment, formed from a focussing optical lens means 32 shown as a compound lens system including solid focussing lens 33, typically made of glass, high molecular weight polymer or the like. Lens 33 is characterized by having an elongated hollow channel or fluid-flow conducting conduit 34 therein directed transversely to the optical axis of lens means 32 and comprising a tubular passage, typically of circular cross-section, through lens 33. At least a portion of such cylindrical conduit, reaction chamber 36, is disposed at the focal region 35 of lens means 32.

Thus, for example assume that fluid containing a ligand that can be excited, per se or through an appropriate tag, into emission such as fluorescence, traverses chamber 36 and is appropriately excited into emission there by excitation radiation focussed onto chamber 36 by lens means 32. That fluorescent emission is then directed by lens means 32 to detector 24 where, assuming that the detector for example is electrical, appropriate electrical signals are produced and can be assessed to evaluate the fluorescence.

Figure 4:
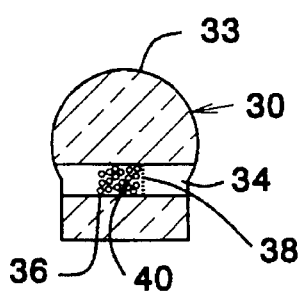
FIG. 4 is a schematic cross-section of a variation of the flow cell of FIG. 2.

In order to provide a better signal-to-ligand ratio, the embodiment shown in FIG. 4 includes mechanical, fluid-porous barrier or screen 38 dimensioned and disposed in conduit 34 adjacent to the focal region 55 of lens means 32 so as to arrest transport of particles or beads 40 of predetermined size in a flow stream through the conduit. Such beads are substantially transparent to both the excitation radiation and the excited fluorescence, and to that end are typically formed of polymethylmethacrylate, styrene-divinylbenzene copolymer or the like. Beads 40 are coated with at least a moiety of the antibody/antigen complex, e.g. a specific-binding ligand, for example an antigen and an antibody thereto, disposed at least on a portion of the surface of the bead.

The mesh or porosity of screen 38 is selected to allow free flow of sample fluid and its constituents therethrough while arresting flow of the coated beads, and thereby accreting a mass of beads 40 against the screen and in the focal region of the lens means 32. The particle size of the beads is selected to be minimized, provided however that when a mass of beads is accreted against screen 38, the sample constituents may still pass freely through the accretion mass. Typically, a bead size that works well with whole blood as a sample is in the range of 50 µm to 250 µm, preferably around 98 µm. Bead size, of course, depends to some extent on the nature of the sample (e.g. blood, food, urine, process stream and the like). Mesh size, of course, depends upon the range of diameters of the beads to be employed in the system, but typically, for beads of about 98 µm diameter, a mesh size of about 50 µm is appropriate. Thus, as sample fluid is flowed through conduit 34, it must pass through the interstices of the accreted mass of coated beads 40, resulting in a very small diffusion distance over which the assayed moiety must pass to complex with the coating on the beads. This small diffusion distance, coupled with the long, tortuous path of the sample through the accreted mass and the high surface to volume ratio of the beads, enables very efficient scavenging of the assayed moiety from the sample. This characteristic of the present invention is significant in as much as the diffusion time is reduced by the square of the diffusion distance. It should also be noted that the entire solid phase is contained in the accreted mass, a very small volume (e.g. about 0.02 cm$^3$ for a typical conduit of 0.18 cm diameter), and is "immersed" in lens 32 thus providing a high numerical aperture, optical coupling between the excitation and detection systems. Because the fluorescent signal is increased by the fourth power of the numerical aperture, high numerical aperture optical coupling is very important.

In operation of the invention shown in FIG. 4, a quantity of beads 40 are preferably preloaded with an appropriate ligand immobilized onto the bead surfaces by adsorption or other known immobilizing techniques and suspended in a suspending fluid. Where the beads will ordinarily not readily form a stable suspension in the suspending fluid, they may be placed into a vortexer (not shown) or similar mixer which maintains the beads in a suspension, typically aqueous, by agitation. A desired potion of the bead suspension is sucked out of the vortexer as by a pump (not shown) and injected into conduit 34 where the flow of the beads is arrested by screen 38, creating an accretion or mass of beads 40 within reaction chamber 36. An aliquot of sample solution being assayed is then flowed through conduit 34 and the mass of beads 40 in reaction chamber 36, effecting the formation of a ligand/conjugate complex on the surface of the beads. As is well known, for competitive assays, prior to flowing the sample solution through the flow cell, typically the sample solution is first treated with a tagging reagent and allowed to incubate. Where the assay is a sandwich assay, the sample solution is passed through the flow cell, then tagged antibody is passed through the cell, and the bead mass is subjected to a wash step. As is well known in the art, a tagged, typically fluorescent, component may be either the complement or conjugate to or an analog of the immobilized ligand, depending upon whether a competitive or sandwich assay is to be performed. The tag or label is typically a fluorescent dye such as a fluorescein dye, acridine dye or the like, all as well known in the art. In either case, the resulting ligand/conjugate complex should include desired dye moieties bound to the complex. Flowing a wash buffer through the bead mass then washes out any unreacted materials and particularly any free dye components, leaving only those dyed moieties as are immobilized on the beads. Light source 22 is then activated to generate excitation light beam 23 (shown in broken lines) which, in turn, is directed to mirror 26 by collimating lens 28 so that the collimated beam is reflected onto lens means 32. The latter focusses the excitation beam to a focal region at which the mass of beads 40 in reaction chamber 36 is located, and the excitation radiation excites the fluorophores on beads 40 into fluorescence. That fluorescence is transmitted through lens 32 and directed through beam splitter mirror 26 to detector 24. After measurements are made, the mass of beads 40 can be readily removed from reaction chamber 36 simply by back-flushing through conduit 34.

As thus described, the technique of filling the reaction chamber from a suspension or pool of preloaded beads is clearly amenable to automation, where the components for specific assays, such as the type of preloaded beads, sample solution, tagging reagent and the like, are selectable by appropriate valves controlling the flow of materials from respective storage containers. However, the present invention also is readily adaptable for more portable systems in which the bead mass and reagents are disposables.

Figure 3:
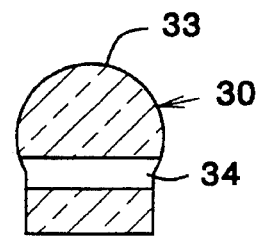
FIG. 3 is a transverse cross-section of the flow cell of FIG. 2.
Figure 5:
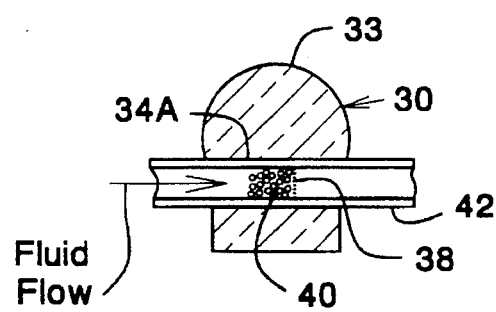
FIG. 5 is a schematic cross-section of another variation of the flow cell of the present invention.

For example, while conduit 34 is shown in FIG. 3 to be simply a passageway through the focal region 55 of lens means 32 transverse to the optical axis 23 of the lens means 32, in the embodiment shown in FIG. 5, conduit 34 is formed of elongated bore 34A of uniform diameter provided similarly rough lens 33 and elongated light-transparent tube 42 having a uniform diameter slightly less than that of bore 34A so that tube 42 may be inserted and removed from the bore. Screen 38 is so disposed within tube 42 that the latter can be positioned within bore 34A adjacent to the focal region of the lens.

Figure 6:
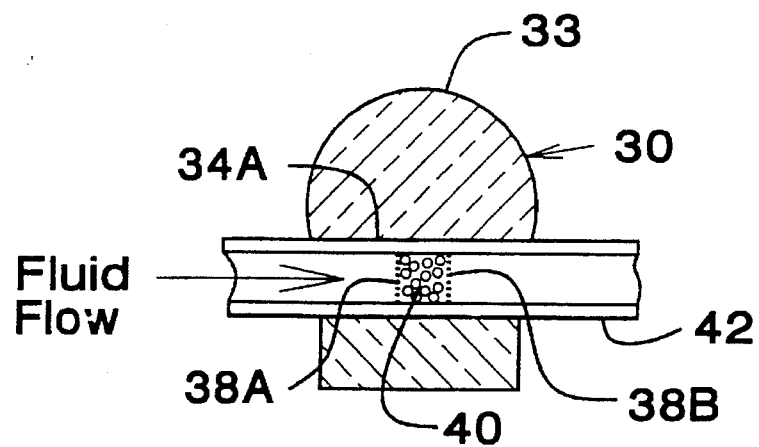
FIG. 6 is a schematic cross-section of a variation of the flow cell of FIG. 5.

In yet another embodiment of the flow cell of the present invention, as shown in FIG. 6, conduit 3, is similarly formed of elongated bore 34A of uniform diameter through lens 33 and elongated light-transparent tube 42A having a uniform diameter slightly less than that of bore 34A so that tube 42 may be inserted and removed from the bore. Screens 38A and 38B are so disposed within tube 42A in spaced-apart relation to one another so as to define reaction chamber 44 within the tube. As in the embodiment of FIG. 5, reaction chamber 44 can be positioned within bore 34A adjacent to the focal region of the lens. Included within chamber 44 is a plurality of beads 40 dimensioned within a specified range of diameters, the mesh of screens being sufficiently smaller than the range of bead diameters so that the latter are trapped by the screens in chamber 44 to form a porous mass positionable substantially at the lens focal region. The beads in the embodiment of FIG. 6 are preferably precoated with the desired specific binding ligand before installation in chamber 44.

In both the embodiments of FIGS. 5 and 6, it will be appreciated that tubes 42A are preferably readily insertable and removable in and from bore 34A as the case may be, hence may be considered to be "disposables". Particularly, the "disposable" shown in FIG. 6 lends itself to laboratory preloading and packaging in hermetically sealed containers from convenient distribution and use. In both the embodiments of FIGS. 5 and 6, the materials forming both lens 32 and tube 42 or 42A are selected so that the respective indices of refraction thereof are substantially matched. In order to provide the optimum optical coupling between tube 42, 42A and lens 32, a refractive index-matching fluid is preferably disposed around the tube in the interspace between the tube and the interior wall of bore 34A.

Figure 7:
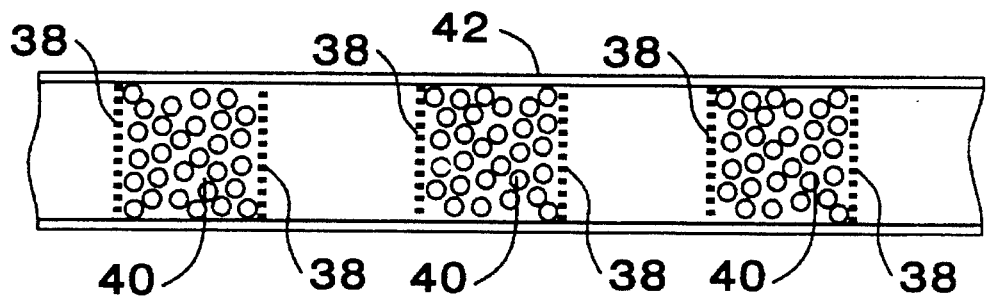
FIG. 7 is a schematic cross-section of another variation of the flow cell of FIG. 5.

It should be understood that bead mass 40 of the embodiment of FIG. 6 can be formed by, for example, the same technique used to create the bead mass of FIG. 5, i.e. by flowing a suspension of beads through tube 42A to accrete against a screen such as 38B, the other screen then being emplaced to capture the bead mass. Alternatively, the porous bead mass may also be formed of a plurality of beads adhered lightly to one another as by sintering or adhesives. For example, the bead mass can be formed by providing a thick layer of beads which may be free-standing, or by coating a porous substrate or forming a sandwich between a pair of porous substrates, with the thick layer of beads, which bead layers include a minor amount of adhesive that will not materially reduce the porosity of the resulting mass. After curing, the coating can be precoated with an appropriate specifically reactive ligand and minute cylinder of the coating punched out and inserted into appropriately dimensioned tubes 42A. Alternatively, sheets of high-molecular weight polymeric material of the desired porosity are commercially available, and after treatment to immobilize the requisite ligand within the porous structure, can be punched to produce the desired cylinders for insertion into tubes 42A. Thus, one may provide a plurality of bead masses, each coated with a different ligand. The resulting plurality of bead masses can be emplaced in a single tube 42A, as shown in FIG. 7, so that one may assay a sample flowing through the tube for several different ligands separately but substantially simultaneously.

Figure 8:
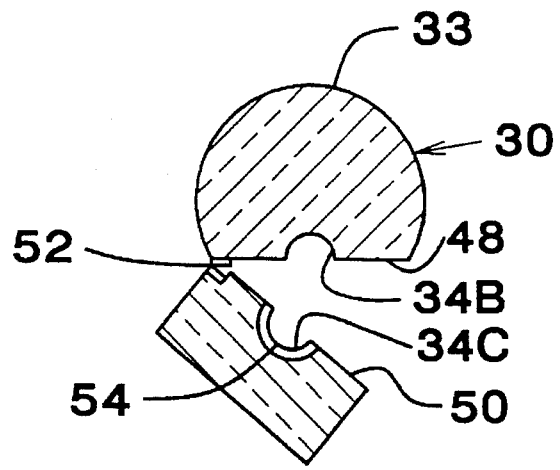
FIG. 8 is a schematic cross-section of yet another embodiment of the flow cell of the present invention.

As shown in FIG. 8, conduit 34 can be formed in part as a shallow elongated channel 34B or hemi-tubular portion of, for example, semicircular cross-section cut or molded into planar surface 48 of lens 33 which extends perpendicularly to the optical axis of the lens and through the focal region of lens means 32. The remainder of conduit 34 is formed by another hemi-tubular elongated channel 34C, similarly of semicircular cross-section, provided in plate 50. The latter is attached to lens 32 adjacent to surface 48, typically by hinging 52 such that plate 50 can be rotated to match channels 34C and 34B into coaxial relation to form a combined conduit of substantially circular cross-section. In the preferred embodiment, the inner surface of channel 34C is provided with highly reflective coating 54.

Since certain changes may be made in the above process and apparatus without departing from the scope of the invention herein involved, it is intended that all matter contained in the above description or shown in the accompanying drawing shall be interpreted in an illustrative and not in a limiting sense.

What is claimed is:

1. An apparatus comprising, in combination:

focussing optical lens means;

a conduit means of substantially uniform cross-sectional dimension disposed within said lens means for fluid flow of a fluid sample therethrough, and extending transversely to an optical axis of said lens means through a focal region of said lens means; and a porous mass of light-transparent material disposed in said conduit means, the porosity of said mass being selected to permit fluid flow of said fluid sample therethrough, said apparatus being arranged and constructed such that said lens means focuses light rays that emanate from said porous mass within said conduit means, said lens means focussing said light rays by refraction.

2. An apparatus comprising, in combination:

focussing optical lens means;

a conduit means of substantially uniform cross-sectional dimension disposed within said lens means for fluid flow of a fluid sample therethrough, and extending transversely to an optical axis of said lens means through a focal region of said lens means; and a porous mass of light-transparent material disposed in said conduit means, the porosity of said mass being selected to permit fluid flow of said fluid sample therethrough, said apparatus being arranged and constructed such that said lens means focuses light rays that emanate from within said conduit means as said light rays exit said lens means.

3. Apparatus as defined in either of claim 1 or claim 2 wherein said lens means comprises a plurality of lenses and said conduit means comprises a cylindrical passage extending through one of said lenses.

4. Apparatus as defined in either of claim 1 or claim 2 including mechanical, fluid-porous barrier means dimensioned and disposed adjacent to said focal region so as to block flow of particulates of predetermined size through said conduit means.

5. Apparatus as defined in either of claim 1 or claim 2 including a first elongated hemi-tubular channel in said lens means and a second elongated hemi-tubular channel in said lens means, said channels being mateable with one another to define said conduit means.

6. Apparatus as defined in claim 5 wherein said second hemi-tubular channel has a light reflective surface on a concave portion thereof.

7. Apparatus as defined in claim 5 wherein one edge of said first channel is hingedly connected to an edge of said second channel.

8. Apparatus as defined in claim 4 wherein said conduit means comprises a cylindrical passage having a light-transparent tube positioned therein, said barrier means being disposed within said tube.

9. Apparatus as defined in claim 4 wherein said barrier means comprises a pair of screens spaced apart from one another so as to define a reaction chamber within said tube; and wherein said porous mass comprises a plurality of particles dimensioned within a specified range of diameters, the mesh of said screens being sufficiently smaller than said range of diameters so that said particles are trapped by said screens in said reaction chamber to form said porous mass positionable substantially at said focal region.

10. Apparatus as defined in claim 8 wherein said lens means and said tube have indices of refraction that are substantially matched.

11. Apparatus as defined in claim 10 including a refractive index-matching fluid disposed around said tube and between said tube and said passage.

12. Apparatus as defined in claim 9 wherein said particles are substantially transparent to light.

13. Apparatus as defined in claim 9 wherein said particles are at least partly coated with at least a moiety of a ligand/conjugate complex.

14. Apparatus as defined in claim 1 or claim 2 wherein said focussing optical lens means comprises a lens having a curved surface with a center of curvature, and wherein said conduit means comprises a passage that extends transversely to said optical axis of said lens, through said focal region of said lens and behind said center of curvature of said lens.

* * * * *

UNITED STATES PATENT AND TRADEMARK OFFICE
CERTIFICATE OF CORRECTION

PATENT NO. : 5,554,340

DATED : September 10, 1996

INVENTOR(S) : Steve J. Lackie

It is certified that error appears in the above-indentified patent and that said Letters Patent is hereby corrected as shown below:

Column 3, line 60: please delete "35"; and insert therefor -- 55 --.

Column 5, line 55: please delete "42"; and insert therefor -- 42A --.

Column 5, line 53: after the words "focal region"; please insert therefor -- 55 --.

Column 6, line 2: after the words "that tubes "; please insert therefor -- 42 and --.

Signed and Sealed this

Fifteenth Day of April, 1997

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,554,340
DATED : September 10, 1996
INVENTOR(S) : Steve J. Lackie

It is certified that error appears in the above-indentified patent and that said Letters Patent is hereby corrected as shown below:

Column 3, line 60: please delete "35"; and insert therefor --55--.

Column 5, line 55: please delete "42"; and insert therefor --42A--.

Column 5, line 64: after the words "focal region"; please insert therefor --55--.

Column 6, line 2: after the words "that tubes "; please insert therefor --42 and--.

This certificate supersedes Certificate of Correction issued April 15, 1997

Signed and Sealed this

Ninth Day of September, 1997

Attest:

BRUCE LEHMAN

Attesting Officer

Commissioner of Patents and Trademarks